United States Patent
Lewer et al.

(10) Patent No.: US 6,800,614 B2
(45) Date of Patent: Oct. 5, 2004

(54) PESTICIDAL MACROLIDES

(75) Inventors: Paul Lewer, Indianapolis, IN (US); Donald R. Hahn, Zionsville, IN (US); Laura L. Karr, Lebanon, IN (US); Paul R. Graupner, Carmel, IN (US); Jeffrey R. Gilbert, Indianapolis, IN (US); Thomas V. Worden, Indianapolis, IN (US); Raymond C. Yao, Carmel, IN (US); Dennis W. Norton, Mooresville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/217,533

(22) Filed: Aug. 13, 2002

(65) Prior Publication Data

US 2003/0186899 A1 Oct. 2, 2003

Related U.S. Application Data

(62) Division of application No. 09/661,065, filed on Sep. 13, 2000, now Pat. No. 6,455,504.
(60) Provisional application No. 60/153,513, filed on Sep. 13, 1999.

(51) Int. Cl.$^7$ .............................................. A01N 43/22
(52) U.S. Cl. ......................... 514/28; 514/29; 424/405; 424/406
(58) Field of Search .............................. 514/25, 27, 28, 514/450, 72; 424/405, 406; 536/7, 1, 17, 2, 18.1; 549/268

(56) References Cited

U.S. PATENT DOCUMENTS

| | | |
|---|---|---|
| 5,362,634 A | 11/1994 | Boeck et al. |
| 5,539,089 A | 7/1996 | Broughton et al. .......... 536/6.5 |
| 6,063,771 A * | 5/2000 | Snyder ....................... 514/31 |
| 6,455,504 B1 * | 9/2002 | Lewer et al. ................. 514/28 |

FOREIGN PATENT DOCUMENTS

| | | |
|---|---|---|
| EP | 0 375 316 | 12/1994 |
| WO | WO 97/00265 | 1/1997 |

* cited by examiner

*Primary Examiner*—Neil S. Levy
(74) *Attorney, Agent, or Firm*—Donald R. Stuart

(57) ABSTRACT

Macrolide compounds produced by culturing Saccharopolyspora species LW107129 (NRRL 30141) have insecticidal and acaricidal activity and are useful intermediates for preparing spinosyn analogs.

5 Claims, No Drawings

PESTICIDAL MACROLIDES

RELATED APPLICATION

This application is a divisional application of Ser. No. 09/661,065 filed Sep. 13, 2000, now U.S. Pat. No. 6,455,504 which claims priority from provisional application Ser. No. 60/153,513 filed Sep. 13, 1999.

FIELD OF THE INVENTION

This invention relates to a new group of natural pesticidal products, and to a novel Saccharopolyspora species that produces the compounds.

BACKGROUND OF THE INVENTION

Fermentation product A83543 is a family of compounds, referred to as spinosyns, that are produced by certain strains of *Saccharopolyspora spinosa*. The previously disclosed naturally produced spinosyns have a 5,6,5-tricylic ring system, fused to a 12-membered macrocyclic lactone, a neutral sugar (rhamnose) and an amino sugar (forosamine) (see Kirst et al. (1991). The known spinosyns have been referred to as factors or components, and each has been given an identifying letter designation, i.e. spinosyn A, B, etc. The compounds are useful for the control of arachnids, nematodes and insects, in particular Lepidoptera and Diptera species, and they are quite environmentally friendly and have an appealing toxicological profile.

U.S. Pat. No. 5,362,634 and corresponding European Patent Application No. 375316 A1 disclose spinosyns A, B, C, D, E, F, G, H, and J. WO 93/09126 discloses spinosyns L, M, N, Q, R, S, and T. WO 94/20518 and U.S. Pat. No. 5,6704,486 disclose spinosyns K, O, P, U, V, W, and Y, and derivatives thereof.

A large number of synthetic modifications to spinosyn compounds have been made, as disclosed in WO 97/00265, but modification of spinosyns at the C-21 position has not been feasible. C-21 of the known compounds is substituted with methyl or ethyl. If means could be found to introduce a reactive functional group in place of the methyl or ethyl group without causing unwanted changes in other portions of the molecule, the way would be opened for synthesis of many additional spinosyn compounds. This has been a long sought and previously unrealized goal of those working in the field of spinosyn synthesis.

SUMMARY OF THE INVENTION

The present invention provides an isolated strain of a novel Saccharopolyspora species designated LW107129 (NRRL 30141).

The invention also provides compounds that can be produced by culturing LW107129 in a suitable culture medium and that have the following general formula 1 or 2:

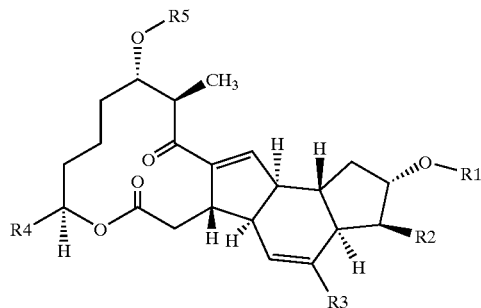

(1)

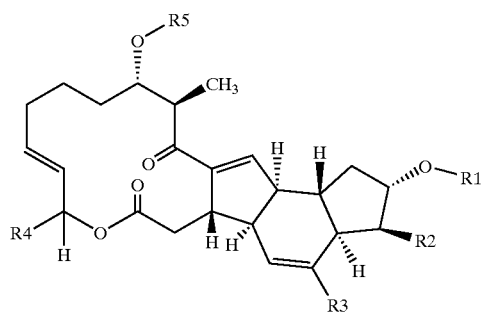

(2)

wherein

R1 is a group of formula 2a, 2b, or 2c

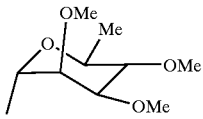

(2a)

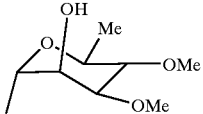

(2b)

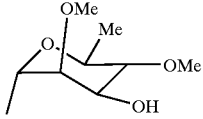

(2c)

R2 is H or OH;

R3 is H or CH$_3$;

R4 in formula 1 is 1-butenyl, 1,3-butadienyl, n-butyl, 3-hydroxy-1-butenyl, or 1-propenyl; and R4 is ethyl in formula 2;

and R5 is H or a group having one of the following formulas 4a through 4i

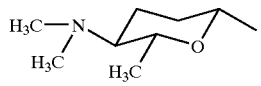

(4a)

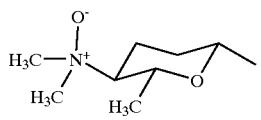

(4b)

-continued (4c)

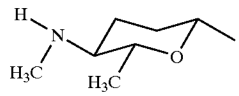

(4d)

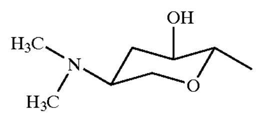

(4e)

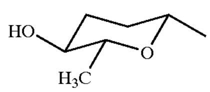

(4f)

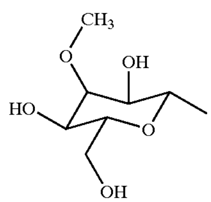

(4g)

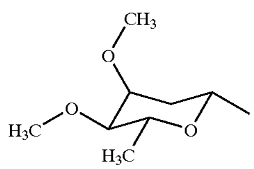

(4h)

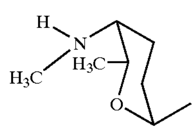

(4i)

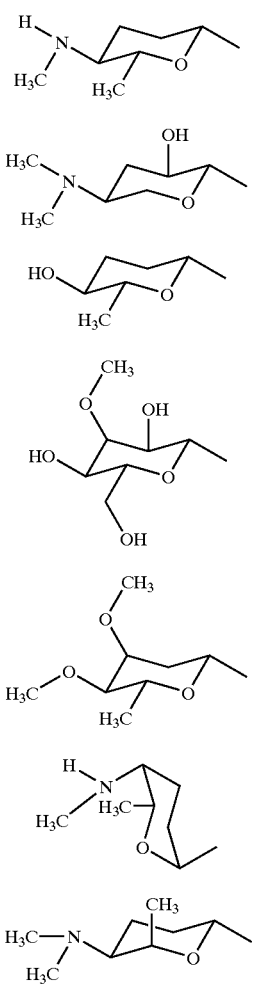

Specific compounds of Formula 1 or 2 that have been prepared and isolated by culturing Saccharopolyspora strain LW107129 are identified in Table I.

TABLE I

| Compound No. | formula | R1 | R2 | R3 | R4 | R5 |
|---|---|---|---|---|---|---|
| 1 | 1 | 2a | H | H | 1-butenyl | 4a |
| 2 | 1 | 2a | H | H | 1-butenyl | 4b |
| 3 | 1 | 2a | H | H | 1-butenyl | 4c |
| 4 | 1 | 2a | H | H | 1-butenyl | 4d |
| 5 | 1 | 2b | H | H | 1-butenyl | 4a |
| 6 | 1 | 2c | H | H | 1-butenyl | 4a |
| 7 | 1 | 2a | H | Me | 1-butenyl | 4a |
| 8 | 1 | 2a | OH | H | 1-butenyl | 4a |
| 9 | 1 | 2a | H | H | 3-hydroxy-1-butenyl | 4a |
| 10 | 1 | 2a | H | H | 3-hydroxy-1-butenyl | 4c |
| 11 | 1 | 2a | H | H | 1,3-butadienyl | 4a |
| 12 | 1 | 2a | H | H | 1-butenyl | 4e |
| 13 | 1 | 2a | H | H | 1-butenyl | 4f |
| 14 | 1 | 2a | OH | H | 1-butenyl | 4e |
| 15 | 1 | 2a | OH | H | 1-butenyl | 4g |
| 16 | 1 | 2a | H | H | 1-propenyl | 4a |
| 17 | 1 | 2a | H | H | 1-butenyl | H |
| 18 | 1 | 2a | H | Me | 1-butenyl | H |
| 19 | 1 | 2a | OH | H | 1-butenyl | H |
| 20 | 1 | 2a | H | H | 3-hydroxy-1-butenyl | H |
| 21 | 1 | 2a | OH | H | 3-hydroxy-1-butenyl | H |
| 22 | 1 | 2a | H | H | 1,3-butadienyl | H |

TABLE I-continued

| Compound No. | formula | R1 | R2 | R3 | R4 | R5 |
|---|---|---|---|---|---|---|
| 23 | 1 | 2a | H | H | n-butyl | H |
| 24 | 1 | 2a | H | H | 1-butenyl | 4h |
| 25 | 1 | 2a | H | H | 1-butenyl | 4i |
| 26 | 1 | 2a | OH | H | 1,3-butadienyl | 4a |
| 27 | 1 | 2a | OH | Me | 1-butenyl | 4a |
| 28 | 1 | 2a | OH | H | 1-propenyl | 4a |
| 29 | 1 | 2b | H | H | 1-butenyl | H |
| 30 | 1 | 2c | H | H | 1-butenyl | H |
| 31 | 2 | 2a | H | H | ethyl | 4a |

All of the components listed in Table I are structurally distinct from previously known spinosyns because, with reference to group R4, no previously known spinosyn compounds have had a 1-butenyl, 3-hydroxy-1-butenyl, 1,3-butadienyl, 1-propenyl, or n-butyl group at C-21 of the macrolide. Further, several of the compounds in Table I differ from all previously known spinosyns because, with reference to group R5, these compounds have new groups linked the oxygen at C-17 on the macrolide. R2 is always H in known spinosyns, therefore variation at this position is novel. Additionally, compound 31 has a new 14-carbon macrolide ring system not previously known in the compounds reported from *S. spinosa.*

The compounds of the invention can react to form salts. Salts that are physiolocally acceptable are also useful in the formulations and methods of this invention. The salts are prepared using standard procedures for salt preparation. For example compounds of the invention can be neutralized with an appropriate acid to form an acid additional salt. The acid addition salts are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

Another aspect of this invention is a process for producing compounds of formula 1 and 2, which comprises culturing Saccharopolyspora strain LW107129 (NRRL 30141) in a suitable medium. The formula 1 and 2 compounds are extracted from the fermentation broth and from the mycelium with polar organic solvents. The compounds may be further purified by techniques well-known in the art, such as column chromatography.

The formula 1 and 2 compounds where R5 is a group having one of the formulas 4a through 4i are useful for the control of mites, ticks, and insects. Therefore, insecticidal and acaricidal compositions and methods for reducing the populations of insects, mites, and ticks using these compounds are also a part of this invention.

Compounds of formula 1 and 2 where R5 is hydrogen (C17-pseudoaglycones) are useful as intermediates in the preparation of insecticidal and miticidal compounds. For example, these compounds can be glycosylated at the C-17 hydroxyl group. The glycosylation may be carried out by chemical synthesis or by microbial bioconversion, using procedures described, for example, in U.S. Pat. No. 5,539,089.

DETAILED DESCRIPTION OF THE INVENTION

Culture Description

The novel strain producing the compounds of the invention has been given the designation LW107129. Culture LW107129 was isolated from a soil sample composed of soils collected at numerous sites. The culture has been deposited in accordance with the terms of the Budapest treaty at the Midwest Area Regional Research Center, Agricultural Research Service, United States Department of Agriculture, 815 North University Street, Peoria, Ill. 61604. The strain was deposited on Jun. 9, 1999, and was assigned deposit number NRRL 30141.

Culture Characteristics

Saccharopolyspora strain LW107129 produces aerial mycelium and bright white spores on the following media: Bennett's, ISP2 and ISP5. Colonies are cream to light tan in color and the substrate mycelium can take on a light brown color, particularly on ISP4 & ISP5. Strain LW107129 does not sporulate on ISP3 and ISP4. No pigments were produced on any medium tested. The mycelium of strain LW107129 undergoes fragmentation in liquid culture.

Morphological Characteristics

Strain LW107129 produces ovid spores in chains of up to 50 spores. The spores are encased in a spore sheath and the spore surface is hairy with infrequent spines.

Physiological Characteristics

Saccharopolyspora strain LW107129 is able to produce acid from the following substrates: D-arabinose, m-erythritol, D-fructose, D-glucose, glycerol, D-mannitol, D-mannose, L-rhamnose, D-ribose and trehalose. Strain LW107129 cannot produce acid from adonitol, L-arabinose, dextrin, dulcitol, ethanol, D-galactose, glycogen, inositol, lactose, maltose, melezitose, melibiose, raffinose, salicin, D-sorbitol, L-sorbose, sucrose, xylitol and D-xylose. Strain LW107129 is able to assimilate several organic acids including acetate, citrate, formate and succinate but not benzoate, butyrate, oxalate or tartrate. Strain LW107129 is able to hydrolyze tyrosine and urea but not adenine, casain, esculin, hippurate, hypoxanthine, starch or xanthifle. LW107129 is resistant to the following antibiotics: carbenicillin, cephalothin, cycloheximide, geneticin, lincomycin, naladixic acid, novobiocin, oxytetracycline, polymixin B, rifampin and spectinomycin and is sensitive to bacitracin, chloramphenicol, erythromycin, hygromycin B, streptomcin, thiostrepton, trimethoprim and vancomycin.

Metabolite Production Method

Formula 1 metabolites are produced by cultivation of strain LW107129 in fermentation media as described below. A culture of LW107129 is inoculated into vegetative media and grown for 4B hours at 30° C. shaking at 250 rpm. Sixty milliliters of this mature first stage vegetative culture is used to inoculate a secondary vegetative culture of 1-liter vegetative medium in a 2-liter culture flask. This culture is incubated at 30° C. for 48 hours shaking at 195 rpm. The mature second stage seed is used to inoculate 70 liters of medium in a stirred tank fermentation vessel, as described in Example 1.

Production of the formula 1 compounds can be followed during the fermentation by testing extracts of the broth. A preferred method for following the production is analysis of the broth extracts by high performance liquid chromatography (HPLC). A suitable system for analysis is described in Example 2.

EXAMPLE 1

Preparation of Metabolites through Fermentation

Metabolites of formula 1 are produced by cultivation of strain LW107129 in fermentation medium as described below. A 1-mL frozen vegetative culture of LW107129 was thawed, inoculated into 100 mL vegetative media in a 500-mL Erlenmeyer flask and grown at 30° C. shaking at 250 rpm for 48 hours.

| Vegetative Medium | |
|---|---|
| Ingredient | Amount (g) |
| Dextrose | 9.0 |
| Trypticase Soy Broth | 30.0 |
| Yeast Extract | 3.0 |
| Magnesium Sulfate. 7 $H_2O$ | 2.0 |
| De-ionized water | 1000.0 |

Sixty milliliters of this mature first stage vegetative culture was used to inoculate a secondary vegetative culture of 1 liter vegetative medium in a 2-liter culture flask. This culture was incubated at 30° C. for 48 hours shaking at 195 rpm. The mature second stage seed was used to inoculate 70 liters of fermentation medium in a stirred tank fermentation vessel.

| Fermentation Medium (per liter of water) | |
|---|---|
| Ingredient | Amount (g) |
| Soybean Flour | 5.0 |
| Dextrose | 10.0 |
| Glycerin | 10.0 |
| Soluble Starch | 5.0 |
| Potato Dextrin | 20.0 |
| Molasses | 10.0 |
| Corn Steep Powder | 5.0 |
| Calcium Carbonate | 3.0 |
| Phytic Acid | 1.0 |
| Magnesium Sulfate | 0.5 |
| Ferric Chloride. 4 $H_2O$ | 0.1 |
| Zinc Chloride | 0.1 |
| Manganese Chloride. 4 $H_2O$ | 0.1 |

Fermentation was maintained at 30° C., 400 rpm for 7–12 days.

Mature fermentation beer can be extracted with a suitable solvent and the metabolites recovered by salt formation and/or chromatographic separation.

EXAMPLE 2

HPLC Assay Method

The following HPLC method is useful for monitoring the fermentation for production of compounds of formula 1 and 2:

Add a volume of denatured ethanol equal to that of an aliquot of fermentation broth. Shake the mixture and allow to stand for a minimum of one hour. Centrifuge the sample to remove bulk cell debris, then microfuge a 1-mL aliquot. The clarified extract is then analyzed by the following HPLC system.

HPLC System:

Column stationary phase: 250-×4.6-mm column, base deactivated silica gel 5-$\mu$m C8 (Hypersil-C8-BDS).

Mobile phase: 10 mm-ammonium acetate-methanol-acetonitrile linear gradient summarized below:

| Time (mins) | Percent solvent A | Percent solvent B |
| --- | --- | --- |
| 0 | 100 | 0 |
| 20 | 0 | 100 |
| 25 | 0 | 100 |
| 30 | 100 | 0 |
| 35 | 100 | 0 | where solvent A is 10 mM ammonium acetate and solvent B is methanol-acetonitrile (1:1)

Flow rate: 1 mL/min

Detection: UV at 250 nm

Retention times of the major factors as summarized below:

| Compound | Retention time (min) |
| --- | --- |
| 7 | 24.6 |
| 1 | 24.2 |
| 3 | 23.7 |
| 12 | 22.9 |
| 15 | 22.8 |
| 18 | 22.6 |
| 8 | 22.5 |
| 17 | 22.2 |
| 13 | 21.6 |
| 14 | 21.4 |
| 19 | 20.2 |
| 20 | 19.3 |
| 21 (both C24-epimers) | 16.2 |

EXAMPLE 3

Isolation of Insecticidally-Active Metabolites from Culture Broth

The following shows how the highest abundance formula 1 compounds were isolated from a typical batch of cultured LW107129. The example gives specific procedures used to isolate compounds 1, 3, 7, 8, 12, 13, 14, 15, 17, 18, 19, 20, and 21. Compounds 2, 4, 5, 6, 9, 10, 11, 16, 22 and 23–31, produced by the organism at lower abundance than the compounds listed above, were isolated using very similar methods applied to larger batches of broth extract. Because the methods are so similar and familiar to one skilled in the art, they are not described in detail here.

The total culture, i.e. cells plus broth, from fermentation of five liters of inoculated medium had a total volume of approximately 3.5 liters after fermentation was complete. This sample was extracted with an equal volume of denatured ethanol by shaking vigorously then allowing to stand at room temperature for two hours. The cell debris was removed by centrifugation and the 7 liters of 50% aqueous ethanol extract was partitioned using dichloromethane (DCM: 2×7 liters). The DCM extract was concentrated to give a pale yellow oil (3.3 g). The oil was dissolved in methanol and divided into two equal aliquots, each of which was chromatographed on a column (4×15 cm; 32–63 µm; Biotage, Inc., U.S.A.) of silica gel. Each column was eluted at 20 mL/min using the following linear solvent gradient then flushed with a final aliquot of solvent G (100 mL):

| time (mins) | solvent type and percentage | | | | | | |
| --- | --- | --- | --- | --- | --- | --- | --- |
| | A | B | C | D | E | F | G |
| 0 | 100 | 0 | 0 | 0 | 0 | 0 | 0 |
| 10 | 0 | 100 | 0 | 0 | 0 | 0 | 0 |
| 15 | 0 | 50 | 50 | 0 | 0 | 0 | 0 |
| 20 | 0 | 50 | 50 | 0 | 0 | 0 | 0 |
| 20.01 | 0 | 0 | 0 | 100 | 0 | 0 | 0 |
| 20 | 0 | 0 | 0 | 0 | 100 | 0 | 0 |
| 40 | 0 | 0 | 0 | 0 | 0 | 100 | 0 |
| 50 | 0 | 0 | 0 | 0 | 0 | 0 | 100 |
| 70 | 0 | 0 | 0 | 0 | 0 | 0 | 100 | where solvent compositions (% by volume) were as follows:

| | A | B | C | D | E | F | G |
| --- | --- | --- | --- | --- | --- | --- | --- |
| hexane | 100% | | | 99.5% | | | |
| toluene | | 100% | 50% | | 99.5% | | |
| ethyl acetate | | | 50% | | | 99.5% | 70% |
| methanol | | | | | | | 20% |
| water | | | | | | | 9.5% |
| diethylamine | | | 0.5% | 0.5% | | 0.5% | 0.5% |

Fractions (30 sec; 10 mL each) were collected throughout the elution. These were analyzed by HPLC according to the procedure described in Example 2 then fractions from each silica gel column profile containing components of similar polarity were pooled, as follows:

| Fraction Numbers | Identifier |
| --- | --- |
| 92–97 | SI-1 |
| 104–112 | SI-2 |
| 114–120 | SI-3 |
| 121–140 | SI-4 |
| flush | SI-5 |

These pooled fractions were dried under vacuum and redissolved in methanol before further fractionation as described below.

Aliquots of fraction SI-1 were applied to a column (250×10 mm; 8 µm particle size) of C-8 reversed phase silica gel (Hypersil-BDS-C8). The applied sample was chromatographed in ammonium acetate (10 mM)-methanol-acetonitrile (30:35:35), eluting at 3 mL/min, collecting 0.75-mL fractions. Fractions containing Compound 17 were pooled and concentrated to dryness to give 14.9 mg pure Compound 17. Fractions containing Compound 18 were pooled and concentrated to dryness to give 1.4 mg pure Compound 18. Fractions containing Compound 12 were pooled and concentrated to dryness to give 4.2 mg pure Compound 12.

Aliquots of fraction SI-2 were applied to a column (250×10 mm; 8 µm particle size) of C-8 reversed phase silica gel (Hypersil-BDS-C8). The applied sample was chromatographed using the ammonium acetate (10 mM)-methanol-acetonitrile linear gradient specified below, eluting at 3 mL/min, collecting 0.75-mL fractions.

| Time (min) | Percent solvent A | Percent solvent B |
|---|---|---|
| 0 | 60 | 40 |
| 5 | 60 | 40 |
| 25 | 0 | 100 |
| 30 | 0 | 100 |
| 32 | 60 | 40 |
| 40 | 60 | 40 |

A = 10 mM ammonium acetate
B = methanol-acetonitrile (1:1)

Fractions containing Compound 20 were pooled and concentrated to dryness to give 11.5 mg pure Compound 20. Fractions containing Compound 19 were pooled and concentrated to dryness to give 3.9 mg pure Compound 19. Fractions containing Compound 14 were pooled and concentrated to dryness to give 2.0 mg pure Compound 14. Fractions containing Compound 13 were pooled and concentrated to dryness to give 4.9 mg pure Compound 13. Fractions containing Compound 15 were pooled and concentrated to dryness to give 2.3 mg pure Compound 15. Fractions containing the two 24-epimeric isomers of Compound 21 were pooled and concentrated to dryness to give 15 mg of a mixture of the two. This mixture was dissolved in methanol and applied to a column (250×10 mm; 8 μm particle size) of C-8 reversed phase silica gel (Hypersil-BDS-C8). The applied sample was chromatographed in ammonium acetate (10 mM)-methanol-acetonitrile (85:7.5:7.5), eluting at 3 mL/min, collecting 3-mL fractions. Fractions containing Compound 21 #1 were pooled and concentrated to dryness to give 9.8 mg pure Compound 21 #1. Fractions containing Compound 21 #2 were pooled and concentrated to dryness to give 4.7 mg pure Compound 21 #2.

Pooled fraction SI-3 was dissolved in methanol and chromatographed on a column (4×7 cm; 32–63 μm; Biotage, Inc., U.S.A.) of silica gel. The column was eluted at 20 mL/min using the following gradient conditions:

| Time (min) | Percent solvent A | Percent solvent B |
|---|---|---|
| 0 | 100 | 0 |
| 5 | 100 | 0 |
| 15 | 60 | 40 |
| 25 | 0 | 100 |
| 40 | 0 | 100 |

A = hexane-diethylamine (99.5:0.5)
B = hexane-isopropanol-diethylamine (75:25:2)

Fractions (80×0.5 min; 10 mL) were collected and 46–50 were pooled and concentrated to dryness. The dried sample was dissolved in methanol and applied to a column (250×10 mm; 8 μm particle size) of C-8 reversed phase silica gel (Hypersil-BDS-C8). The applied sample was chromatographed in ammonium acetate (10 mM)-methanol-acetonitrile (20:40:40), eluting at 3 mL/min, collecting 0.75-mL fractions. Fractions containing Compound 1 were pooled and concentrated to dryness to give 24.3 mg pure Compound 1. Fractions containing Compound 7 were pooled and concentrated to dryness to give 1.5 mg pure Compound 7.

Pooled fraction SI-4 was dissolved in methanol and applied to a column (250×10 mm; 8 μm particle size) of C-8 reversed phase silica gel (Hypersil-BDS-C8) The applied sample was chromatographed in the following linear gradient elution system, at a flow rate of 5 mL/min, collecting 88×1.25 mL fractions:

| Time (mins) | Percent solvent A | Percent solvent B |
|---|---|---|
| 0 | 100 | 0 |
| 20 | 0 | 100 |
| 25 | 0 | 100 |
| 30 | 100 | 0 |
| 35 | 100 | 0 |

A = 10 mM ammonium acetate
B = methanol-acetonitrile (1:1)

Fractions containing crude Compound 1 were pooled and concentrated to dryness, as were fractions containing crude Compound 8. The pooled, dried fractions from above were each dissolved in methanol and re-chromatographed on a column (250×10 mm; 8 μm particle size) of C-8 reversed phase silica gel (Hypersil-BDS-C8). The samples were eluted using ammonium acetate (10 mM)-methanol-acetonitrile (20:40:40), eluting at 3 mL/min, collecting 0.75-mL fractions. Fractions containing Compound 8 were pooled and concentrated to dryness to give 5.8 mg pure Compound 8. Fractions containing Compound 1 were pooled and concentrated to dryness to give a further 7.3 mg pure Compound 1.

The dried column flush fraction SI-5 was dissolved in methanol and applied to a column (250×10 mm; 8 μm particle size) of C-8 reversed phase silica gel (Hypersil-BDS-C8). The applied sample was chromatographed in ammonium acetate (10 mM)-methanol-acetonitrile (20:40:40), eluting at 3 mL/min, collecting 0.75-mL fractions. Fractions containing Compound 7 were pooled and concentrated to dryness to give 3.5 mg pure Compound 7.

Spectroscopic Characteristics

The chemical structures of the new components were determined by spectroscopic methods, including nuclear magnetic resonance spectroscopy (NMR), mass spectrometry (MS), ultraviolet spectroscopy (UV) and by comparison to spinosyn A and D and related analogs. The following paragraphs describe the spectroscopic properties of the components described above. In this discussion, a detailed analysis of the spectroscopic properties of Compound 1 is given. This is then followed by a discussion of the spectroscopic features for the other related components enabling one skilled in the art to conclude the chemical structure by comparison with the data for Compound 1. For the convenience of the reader, the following diagram of Compound 1 provides the position designations of all NMR spectral data for the natural factors presented below:

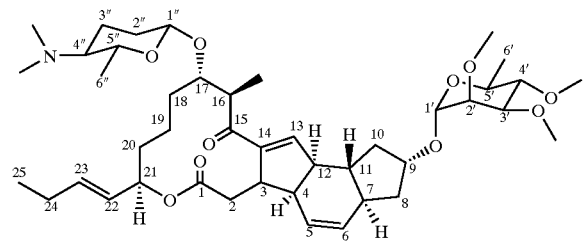

Compound 1 has the following characteristics:
Molecular weight: 757
Molecular formula: $C_{43}H_{67}NO_{10}$
UV (by diode array detection during LC analysis, solvent=methanol-acetonitrile (1:1)): 244 nm
Electrospray MS: m/z for $[M+H]^+$=758.5; forosamine sugar fragment ion at m/z 142.1.
Accurate ESI-MS: m/z for $[M+H]^+$=758.4845+/−0.0007 (theory: 758.4843).
Table II summarizes the $^1H$ and $^{13}C$ NMR spectral data for Compound 1 in $CDCl_3$.

TABLE II

Chemical Shift Data for Compound 1 ($CDCl_3$)

| Position | 1H | 13C |
|---|---|---|
| 1 | — | 172.1 |
| 2 | 3.14 | 34.5 |
|   | 2.39 |   |
| 3 | 3.02 | 47.6 |
| 4 | 3.42 | 41.3 |
| 5 | 5.79 | 128.7 |
| 6 | 5.87 | 129.3 |
| 7 | 2.16 | 41.1 |
| 8 | 1.92 | 36.2 |
|   | 1.35 |   |
| 9 | 4.30 | 76.0 |
| 10 | 2.26 | 37.3 |
|   | 1.34 |   |
| 11 | 0.90 | 46.0 |
| 12 | 2.86 | 49.4 |
| 13 | 6.77 | 147.5 |
| 14 | — | 144.1 |
| 15 | — | 202.8 |
| 16 | 3.31 | 47.4 |
| 17 | 3.66 | 80.8 |
| 18 | 1.60 | 34.2 |
| 19 | 1.80 | 21.4 |
|   | 1.23 |   |
| 20 | 1.60 | 31.6 |
| 21 | 5.04 | 76.3 |
| 22 | 5.30 | 128.0 |
| 23 | 5.66 | 134.9 |
| 24 | 1.99 | 25.0 |
| 25 | 0.95 | 13.1 |
| 26 | 1.20 | 16.3 |
| 1' | 4.86 | 95.4 |
| 2' | 3.50 | 77.7 |
| 2'-OMe | 3.48 | 59.0 |
| 3' | 3.46 | 81.0 |
| 3'-OMe | 3.48 | 57.6 |
| 4' | 3.11 | 82.2 |
| 4'-OMe | 3.56 | 60.9 |
| 5' | 3.55 | 67.9 |
| 6' | 1.28 | 7.8 |
| 1" | 4.42 | 103.6 |
| 2" | 1.98 | 30.9 |
|    | 1.46 |    |
| 3" | 1.86 | 18.3 |
|    | 1.50 |    |
| 4" | 2.22 | 64.8 |
| 4"-NMe$_2$ | 2.23 | 40.7 |
| 5" | 3.50 | 73.7 |
| 6" | 1.26 | 18.9 |

Chemical shifts referenced to TMS at 0 ppm

Distinguishing NMR spectroscopic features of other metabolites were as follows:

The NMR spectra of structures having the base macrolide structure of Compound 7 were exemplified by the absence of the proton signals at 5.8 and 5.7 ppm, and by the presence of a new olefinic resonance at 5.5 ppm. Additionally, a methyl resonance at 1.7 ppm indicated the presence of an olefinic methyl group. The NMR spectra of structures having the base macrolide structure of Compound 8 were exemplified by a number of features. H-8 appeared as a doublet at 4.15 ppm, and H-9 appeared at 4.1 ppm (dd). There was no measurable coupling constant between H-8 and H-9. The signal for H-11 moved downfield to 1.5 ppm. Hydroxylation at C-24 in any of these 21-butenyl structures was indicated by a downfield shift of both H-24 and H-25, which appeared as a multiplet and triplet, respectively. Concurrently, H-23 changed to a double doublet. The NMR spectra of structures having the base macrolide structure of Compound 11 were exemplified by the addition of olefinic resonances at 5.1, 5.25, and 5.6 ppm, with coupling patterns consistent with a terminal olefin group. Additionally, the signal indicative of a terminal aliphatic methyl group at 0.9-1.0 ppm was absent. The NMR spectra of compounds having the base macrolide structure of Compound 16 were exemplified by the downfield shift of H-24 and the collapse of the triplet structure to a doublet at approx. 1.4 ppm. In these cases, H-23 changed to a doublet of quartets, and analysis of a 2D COSY spectrum indicated coupling of this doublet to the other olefinic proton, indicating the presence of a propenyl group. The NMR spectra of compounds having the base macrolide structure of Compound 23 were exemplified by the absence of the butenyl olefinic protons and were distinguished from the previously known spinosyns by examination of 2D COSY and TOCSY experiments. Analysis of the coupling pathway arising from H-25 indicated a 4-carbon butyl group connected to C-21. The glycoside substructures attached to the oxygen at C-17 were identified using a variety of 2-dimensional NMR experiments.

The methyl triplet H-25 and H-24 of the expanded ring macrolide 31 resembled the ethyl group in spinosyn A. Additionally, H-21 moved upfield to 4.8 ppm, relative to its position in compound 1. However, the olefinic protons were still present. A 2D COSY spectrum showed that both the ethyl group and the olefin were coupled to H-21 indicating that the double bond in this compound was within the ring. This was consistent with this compound being an isomer of compound 1, based on its molecular weight being 758, from the mass spectrum.

A list of all metabolites with the molecular adduct ion observed in ESI-MS, from which the molecular weight was deduced, is shown in Table III:

TABLE III

| Compound No. | Key Mass Spectral Data[1] (m/z) |
|---|---|
| 1 | 758.5 $[M + H]^+$ |
| 2 | 774.5 $[M + H]^+$ |
| 3 | 744.5 $[M + H]^+$ |
| 4 | 774.4 $[M + H]^+$ |
| 5 | 744.8 $[M + H]^+$ |
| 6 | 744.8 $[M + H]^+$ |
| 7 | 772.5 $[M + H]^+$ |
| 8 | 774.5 $[M + H]^+$ |
| 9 | 774.7 $[M + H]^+$ |
| 10 | 760.5 $[M + H]^+$ |
| 11 | 756.5 $[M + H]^+$ |
| 12 | 748.5 $[M + NH_4]^+$ |
| 13 | 810.5 $[M + NH_4]^+$ |
| 14 | 764.5 $[M + NH_4]^+$ |
| 15 | 808.5 $[M + NH_4]^+$ |
| 16 | 744.5 $[M + H]^+$ |
| 17 | 617.4 $[M + H]^+$ |
| 18 | 631.4 $[M + H]^+$ |
| 19 | 633.4 $[M + H]^+$ |
| 20 | 650.4 $[M + NH_4]^+$ |
| 21[2] | 666.4 $[M + NH_4]^+$ |

TABLE III-continued

| Compound No. | Key Mass Spectral Data[1] (m/z) |
|---|---|
| 22 | 615.4 [M + H]$^+$ |
| 23 | 636.5 [M + NH$_4$]$^+$ |
| 24 | 744.4 [M + H]$^+$ |
| 25 | 758.4 [M + H]$^+$ |
| 26 | 772.4 [M + H]$^+$ |
| 27 | 788.7 [M + H]$^+$ |
| 28 | 760.4 [M + H]$^+$ |
| 29 | 620.3 [M + NH$_4$]$^+$ |
| 30 | 620.3 [M + NH$_4$]$^+$ |
| 31 | 758.4 [M + H]$^+$ |

[1]Molecular adduct ions observed using LC/MS with electrospray ionization.
[2]Two isomers, both had same MS characteristics Insecticide and Acaricide Activity Compounds of the invention (other than those wherein R5 is H) are useful for the control of insects, mites, and ticks. Therefore, a further aspect of the present invention is directed to methods for inhibiting an insect, mite, or tick which comprises applying to the locus of the insect, mite, or tick, an insect-, mite-, or tick-inhibiting amount of a compound of formula 1 or 2 wherein R5 is a group having one of the formulas 4a through 4i.

The "locus" of the insect, mite, or tick refers to the environment in which the insect, mite, or tick lives or where its eggs are present, including the air surrounding it, the food it eats, or objects which it contacts. For example, plant-ingesting insects or mites can be controlled by applying the active compound to plant parts which the insects or mites eat or inhabit, particularly the foliage.

By the term "inhibiting an insect, mite, or tick" it is meant that there is a decrease in the number of living insects, mites or ticks, or a decrease in the number of eggs. The extent of reduction accomplished by a compound depends, of course, on the application rate of the compound, the particular compound used, and the target insect, mite, or tick species. At least an insect-inactivating, mite-inactivating, or tick inactivating amount should be used. By "inactivating amount" it is meant that an amount of compound is used to cause measurable reduction in the treated insect, mite, or tick population. Typically from about 1 to about 1,000 ppm (or 0.01 to 1 Kg/acre) of compound is used.

The compounds show activity against a number of insects, mites, and ticks. More specifically, the compounds show activity against members of the insect order Lepidoptera such as the beet armyworm, tobacco budworm, codling moth and cabbage looper. Other typical members of this order include the southern armyworm, cutworms, clothes moths, Indian meal moth, leaf rollers, corn earworm, cotton bollworm, European corn borer, imported cabbage worm, pink bollworm, bagworms, Eastern tent caterpillar, sod webworm, and fall armyworm.

The compounds also show activity against members of the order Coleoptera (the beetles and weevils such as the Colorado potato beetle, spotted and striped cucumber beetles, Japanese beetle, and boll weevil) and Diptera (the true flies such as the house fly, mosquitoes, fruit flies, stable and horn flies, and leaf miners)

The compounds also show activity against members of the order Hempitera (true bugs such as plant bugs, stink bugs, and chinch bugs), Homoptera (such as the aphids, leafhoppers, planthoppers, whiteflies, scales, and mealybugs), Mallophaga (chewing lice), Anoplura (sucking lice), Thysanoptera (thrips), Orthoptera (such as cockroaches, grasshoppers, and crickets), Siphonaptera (fleas), Isoptera (termites), and members of the Hymenoptera order Formicidae (ants).

The compounds also show activity against mites and ticks of the order Acari, for example, the two-spotted spider mite. Other typical members of this order include plant parasites such as the citrus red mite, European red mite, and citrus flat mite, and animal parasites such as the mange mite, scab mite, sheep scab mite, chicken mite, scalyleg mite, depluming mite and dog follicle mite.

Specific representative antrhopod pests which can be controlled by the present compounds include the following: *Amblyomma americanum* (Lone-star tick), *Amblyomma maculatum* (Gulf Coast tick), *Argas persicus* (fowl tick), *Boophilus microplus* (cattle tick), Chorioptes spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick) *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), *Sarcopces scabiei* (mange mite), Aedes (mosquitoes), Anopheles (mosquitoes), Culex (mosquitoes), Culiseta, *Bovicola bovis* (cattle biting louse), *Callitroga homnivorax* (blowfly), Chrysops spp. (deer fly), *Cimex lectularius* (bed bug), Cochliomyia spp. (screwworm), *Ctenocephalides canis* (dog flea), *Ctenocephalides felis* (cat flea), Culicoides spp. (midges, sandflies, punkies, or no-see-ums), *Damalinia ovis* (sheep biting louse), Dermatobia spp. (warble fly), *Gasterophilus haemorrhoidalis* (nose bot fly), *Gasterophilus intestinalis* (common horse bot fly), *Gasterophilus nasalis* (chin fly) Glossina spp. (tsetse fly), *Haematobia irritans* (horn fly, buffalo fly), *Haematopinus asini* (horse sucking louse), *Haematopinus eurysternus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), Lucilia spp. (maggot fly), *Melophagus ovinus* (sheep ked), Musca spp. (house fly, face fly), *Oestrus ovis* (nose bot fly), Pediculus spp. (lice), Phlebotomus spp. (sandfly), *Phormia regina* (blowfly), Psorophora spp. (mosquito), Pthirus spp. (lice), Reduvius spp. (assassin bug), Simulium spp. (black fly), *Solenopotes capillatus* (little blue cattle louse), *Stomoxys calcitrans* (stable fly) Tabanus spp. (horse fly), Tenebrio spp. (mealworms), Triatoma spp. (kissing bugs)

The compounds are useful for reducing populations of insects, mites, and ticks and are used in a method of inhibiting an insect, mite, or tick population which comprises applying to a locus of the insect, mite or tick an effective insect-, mite-, or tick-inactivating amount of an active compound of the invention. In one preferred embodiment, the present invention is directed to a method for inhibiting a susceptible insect of the order Lepidoptera that comprises applying to a plant an effective insect-inactivating amount of an active compound of the invention. Another preferred embodiment of the invention is directed to a method of inhibiting biting flies of the order Diptera in animals which comprises administering an effective pest-inhibiting amount of a compound orally, parenterally, or topically to the animal. Another preferred embodiment of the invention is directed to a method of inhibiting mites or ticks of the order Acarina which comprises applying to the locus of the mite or tick a mite- or tick-inactivating amount of an active compound of the invention.

Not only are the compounds disclosed herein useful in producing agricultural products, acid addition salts of these compounds, where possible, are also useful products. These salts are useful, for example, in separating and purifying the formula 1 and 2 compounds. In addition, some of these salts may have increased water-solubility. Acid addition salts may be prepared from the compounds disclosed in Formula 1 where R5 is a basic nitrogen-containing sugar molecule such as forosamine. The salts of the compounds are prepared using standard technology for preparing salts which are well known to those skilled in the art. Acid addition salts that are particularly useful include, but are not limited to, salts formed by standard reactions with both organic and inorganic acids such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

EXAMPLE 4

Insect Screens

A. Tobacco Budworm (*Heliothis virescens*) Neonate Drench Assay

To compare insecticidal activities of formula 1 compounds in neonate (<6 hr post-eclosion) larval *Heliothis virescens*, 1 µg/µL acetone solutions of each of the metabolites were first prepared. The acetone solutions were then diluted with Millipore $H_2O$ containing 0.025% Triton X-100 surfactant to yield treatments of 25 or 50 ppm. One milliliter of either concentration of each metabolite was then pipetted directly over and onto a 100-mm diameter #1 Whatman qualitative filter paper circle upon which 20 tobacco budworm neonate larvae had been gently placed. Each treated filter paper and its associated larvae was then placed in a 20 mm×100 mm disposable plastic petri plate. One-hour later, a 1 $cm^3$ portion of agar-based lepidoptera diet (modified Shorey diet, Southland Products, Lake Village, Ark.) was placed into each plate as a larval food source. The petri plates are held at 27° C. for 24 hr and then percent larval mortality in each treatment was determined. Results are presented hereinafter in Table IV.

B. Beet Armyworm (*Spodoptera littoralis*) Topical Assay

An additional measure of the relative insecticidal activities of the formula 1 compounds was generated by using a 1 µg/µL methanol solution of each compound applied at 1 µL per larva of laboratory-reared *Spodoptera littoralis*, (mean wt of 43 mg). Each compound was applied along the dorsum of each of six larvae. Treated larvae then held for five days at 21° C., 60% RH in six-well plastic culture plates. Larvae were each supplied with a 1 $cm^3$ of agar-based lepidoptera diet for sustenance during the 5-day post-exposure interval. Percent mortality was determined at the end of a five day period. Results are presented in Table IV.

TABLE IV

| Compound | Tobacco Budworm Neonate Drench (24 hr) | | Beet Armyworm Topical (120 hr) | |
|---|---|---|---|---|
| | Rate (ppm) | Mortality (%) | Rate (ug/larva) | Mortality (%) |
| 1 | 50 | 100 | 1 | 100 |
| 2 | 50 | 100 | 1 | 100 |
| 3 | — | NT | 1 | 100 |
| 4 | 50 | 100 | 1 | 100 |
| 5 | — | NT | — | NT |
| 6 | — | NT | — | NT |
| 7 | 50 | 100 | 1 | 100 |
| 8 | — | NT | 1 | 100 |
| 9 | 50 | 100 | 1 | 33 |
| 10 | 50 | 100 | 1 | 0 |
| 11 | 50 | 100 | 1 | 100 |
| 12 | 50 | 100 | 1 | 50 |
| 13 | 25 | 45 | 1 | 0 |
| 14 | 25 | 100 | — | NT |
| 15 | 25 | 100 | 1 | 67 |
| 16 | 50 | 100 | 1 | 100 |
| 17 | 25 | 10 | 1 | 0 |
| 18 | 25 | 0 | 1 | 0 |
| 19 | 25 | 93 | 1 | 0 |
| 20 | 25 | 20 | 1 | 0 |
| 21 #1 | 25 | 4 | 1 | 0 |
| 21 #2 | 25 | 7 | 1 | 0 |
| 23 | — | NT | — | NT |
| 24 | 50 | 100 | 1 | 50 |
| 25 | 50 | 100 | 1 | 17 |
| 26 | 50 | 100 | 1 | 100 |
| 27 | 50 | 100 | 1 | 100 |
| 28 | 50 | 100 | 1 | 17 |
| 29 | — | NT | — | NT |
| 30 | — | NT | — | NT |
| 31 | 50 | 100 | 1 | 100 |

Insecticidal Compositions

The compounds are applied in the form of compositions, which are also a part of this invention. These compositions comprise an insect- or mite-, or tick-inactivating amount of a compound of the invention in a phytologically acceptable inert carrier. The active ingredient(s) may be present as a single compound, a mixture of two or more compounds or a mixture of one or more compounds of the invention together with the dried portion of the fermentation medium in which it is produced.

Compositions are prepared according to the procedures and formulas which are conventional in the agricultural or pest control art, but which are novel and important because of the presence of one or more of the compounds of this invention. The compositions may be concentrated formulations which are dispersed in water or may be in the form of a dust, bait or granular formulation used without further treatment.

The dispersions in which the compounds or crude dried material are applied are typically aqueous suspensions or emulsions prepared from concentrated formulations of the compounds or crude material. The water-soluble or water-suspension or emulsifiable formulations are either solids, wettable powders, or liquids, known as emulsifiable concentrates or aqueous suspensions. Wettable powders may be agglomerated or compacted to form water dispersible granules. These granules comprise mixtures of compound or crude dried material, inert carriers and surfactants. The concentration of the compound or crude dried material is typically between about 0.1% to about 90% by weight. The inert carrier is typically attapulgite clays, montmorillonite clays and the diatomaceous earths or purified silicates.

Surfactants comprise typically about 0.5% to about 10% of the wettable powder, where the surfactants are typically sulfonated lignins, condensed napthalene-sulfonates, the napthalene-sulfonates, alkyl-benenesulfonates, alkysulfonates or nonionic surfactants such as ethylene oxide adducts of alkylphenols or mixtures thereof.

Emulsifiable concentrates of the claimed compounds typically range from about 50 to about 500 grams of compound per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents -rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble compounds of this invention, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants as discussed herein. Inert ingredients such as inorganic salts and synthetic or natural gums may also be employed to increase the density and/or viscosity of the aqueous vehicle as is desired.

Precipitated flowables may be prepared by dissolving the active molecule in a water-miscible solvent and surfactants or surface-active polymers. When these formulations are mixed with water, the active compound precipitates with the surfactant controlling the size of the resulting microcrystalline precipitate. The size of the crystal can be controlled through the selection of specific polymer and surfactant mixtures.

The compounds may also be applied as a granular composition that is applied to the soil. The granular composition typically contains from about 0.5% to about 10% by weight of the compound. The compound is dispersed in an inert carrier which is typically clay or an equivalent substance. Generally, granular compositions are prepared by dissolving the compound in a suitable solvent and applying it to a granular carrier which has been preformed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The compounds may also be combined with an appropriate organic solvent. The organic solvent is typically a bland petroleum oil that is widely used in the agricultural industry. These combinations are typically used as a spray. More typically, the compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The amount of compound applied to the loci of insects, mites, and ticks is not critical and can easily be determined by those skilled in the art. Generally, concentrations of from about 10 ppm to about 5,000 ppm of the compounds provide the desired control. For crops such as soybeans and cotton, the rate of application is about 0.01 to about 1 kg/ha, where the compound is applied in a 5 to 50 gal/A spray formulation. The compounds may be applied to any locus inhabited by an insect, mite, or tick. Such locus typically is cotton, soybean and vegetable crops, fruit and nut trees, grape vines, houses and ornamental plants.

The compounds of the present invention are also useful for the treatment of animals to control arthropods, i.e., insects and arachnids, which are pests on animals. These arthropod pests typically attack their hosts on the external ("ecto") surface; agents which control such pests are referred to as "ectoparasiticides". All animals are subject to attack by such pests, though the problems are most severe among vertebrate hosts. Human beings are potential hosts for many parasites, and in tropical areas and in areas with minimal sanitation, parasitic infections are a regular problem in medical practice. Also highly subject to attack by parasites are the numerous livestock animals, such as cattle, sheep, pigs, goats, buffalo, water buffalo, deer, rabbits, chickens, turkeys, ducks, geese, ostriches, and the like. Horses and other pleasure animals are subject to parasitic attack, as are mink and other animals grown for their fur, and rats, mice and other animals used in laboratory and research settings. Companion animals such as dogs and cats are highly subject to attack by parasites, and because of their close relationship with humans, such parasitism poses problems for the humans with whom they are associated. Fish, crustacea, and other aquatic species are also subject to parasitic attack. In short, parasitism involves as hosts essentially the whole range of animals.

The economic toll from ectoparasitic infestations is large. In the livestock realm, animals suffer reduced feed efficiency and growth rates. Milk and wool production suffer, and there is damage to fleece, hides, and pelts. Animals are rendered susceptible to secondary microbiological infections and to further parasite attack. Ectoparasites also cause considerable discomfort even when they are not severely detrimental to health and production.

Although a number of parasiticides are in use, they suffer from a variety of problems, including a limited spectrum of activity, environmental toxicity, the need for repeated treatment, and, in many instances, resistance by ectoparasites. Therefore, there is a continuing need for new ectoparasiticides.

The compounds of the invention provide a new tool in the armamentarium for controlling ectoparasites. In this embodiment, the present invention is directed to a method for inhibiting or killing an arthropod pest on a host animal, which comprises contacting the pest with an effective amount of a compound of the present invention.

The present compounds' ectoparasiticidal activity is achieved when the compounds contact the pests. The contact can be of the egg, larvae, adult, or other life stage. "Contact" includes ingestion of the compound by the pest.

EXAMPLE 5

In vivo Mouse/Adult Stable Fly (ASF) Assay

On Study Day 0, six, thirty-gram, white laboratory mice (*Mus musculus*) (8–10 week old, ICR females, Harlan-Sprague-Dawley, Inc., Indianapolis, Ind.) per treatment were dosed with test article or solvent (90% ethyl oleate/10% DMSO), either orally or topically. On Study Day 1, two mice from each treatment were anesthetized with a 0.25 mL intramuscular injection of a combination of 1.0 mL ketamine (Fort Dodge, Ketaset®, ketamine HCl injection, 100 mg/mL) and 1.0 mL xylazine (Bayer, Rompun®, 20 mg/mL injectable) in 4.5 mL sterile water. The anesthetized mice were placed in the fly boxes containing 30 adult stable fly. The anesthetized mice were left in the boxes for up to 60 minutes and the flies allowed to obtain a blood meal undisturbed. After removal from the fly boxes, the unconscious mice were immediately euthanized with $CO_2$. The fly boxes were exposed to a 12-our day/12-hour night cycle for the entire study period. The temperature in the assay room was 68–72° F. and the humidity was 50–60%. These procedures were repeated exactly on Study Days 2 and 3 with the remaining treated mice. Each day the number of dead flies was recorded and fly boxes discarded. Total percent fly mortality was determined for each treatment and compared to fly mortality of continuously fed ASF and ASF fed on solvent treated control mice. Results of testing compounds 1 and 8 are as follows:

| treatment | % motrality | | | |
|---|---|---|---|---|
| | Day 1 | Day 2 | Day 3 | Total |
| solvent 100 mg/kg | 6 | 10 | 10 | 10 |
| Compound 1 | 16 | 53 | 86 | 86 |
| Compound 8 | 13 | 46 | 76 | 76 |

EXAMPLE 6

In vitro Tick Larval Packet Test (LPT) Assay

Titrated levels of experimental compounds were dissolved in a combination of olive oil and trichloroethylene and pipetted onto squares of laboratory filter paper After allowing about an hour for the trichloroethylene to evaporate, the filter papers were folded in half and two sides secured with clamps, forming packets.

Approximately, 100 larval ticks (*Amblyomma americannum*) were placed inside each packet and the remaining open side secured with a clamp. The packets were incubated for 24 hours at approximately 72° F. and 95% humidity. Each packet was opened separately and the number of live and dead larvae determined. Percent mortality was determined for each compound. Results of testing Compounds 1 and 8 are as follows:

| Compound | 0.5%/5000 ppm | 0.1%/1000 ppm | 0.05%/500 ppm |
|---|---|---|---|
| 1 | 100% | 100% | 93.58% |
| 8 | 100% | 69.87% | 12.47% |

EXAMPLE 7

In vitro Adult Stable Fly Assay

Dental wicks were saturated with serum containing titrated levels of experimental compounds starting at 100 ppm. The dental wicks were placed in petri dishes along with 10 adult stable flies (*Stomoxys calcitrans*) previously chilled for easier handling. Percent mortality was determined after 24 and 48 hours incubation at approximately 25° C. and 75–85% humidity when compared to a dish containing a wick with control serum only.

Results of testing compounds 1 and 8 are as follows:

| | | % mortality | | | |
|---|---|---|---|---|---|
| Cmpd | Day | 5.0 ppm | 1.0 ppm | 0.5 ppm | 0.1 ppm |
| 1 | 24 hr | 60 | 10 | 20 | 10 |
| | 48 hr | 70 | 30 | 20 | 10 |
| 8 | 24 hr | 90 | 30 | 10 | 0 |
| | 48 hr | 100 | 80 | 10 | 0 |

EXAMPLE 8

In vitro Larval Blow Fly Assay

Filter inserts were placed individually in 96-well microtiter plates. Each insert was saturated with bovine serum combined with titrated levels of experimental compounds starting at 100 ppm. Approximately 30 larval blowfly (*Phormia regina*) were placed each well and the entire plate sealed. The plates were incubated for up to 48 hours incubation at approximately 25° C. and 75–85% humidity after which efficacy was determined by visual inspection of each well for larvae movement. The results of testing compounds 1 and 8 are as follows (both compounds were active above 5 ppm):

| Cmpd | 5 ppm | 2.5 ppm | 1.25 ppm | 0.62 ppm | 0.31 ppm | 0.15 ppm |
|---|---|---|---|---|---|---|
| 1 | A | A | A | N | N | N |
| 8 | A | N | N | N | N | N |

A indicates mortality as indicated by absence of larvae movement.
N indicates that larvae movement was observed.

Techniques for delivering ectoparasiticides are well known to those skilled in the art. In general, a present compound is applied to the exterior surface of an animal, whereby it contacts pests already present on the host as well as those which arrive on the host's body within the efficacy period of the compound. Typically, the compound is formulated in a liquid formulation which is sprayed onto the animal's surface or poured onto the animal's surface. Another conventional treatment is a "dip", whereby cattle are treated by being substantially immersed in a dilute solution of an ectoparasiticide. For some hosts and pests, the formulation can be a dust, which is sprinkled onto the host, or a shampoo or cream which is employed in bathing the animal. Collars on cats and dogs are also employed as a way of delivering an ectoparasiticide directly to the animal's surface.

In another embodiment, the compounds of the invention can be delivered to animals using ear tags, a delivery method disclosed in U.S. Pat. No. 4,265,876.

In another technique, an ectoparasiticide is applied to locations frequented by animals, so that pests are thereby contacted by the compound even as in direct application to the host. Application to pet bedding is well known, as is application to carpeting. For cattle, dusting bags are well known. These are positioned in a doorway where the cattle inevitably rub against the bag and pests are contacted by the present compound.

In yet another embodiment, the present compounds can be used to control anthropod pests in the feces of cattle and other animals. In this embodiment, the compounds are administered orally and the compounds travel through the intestinal tract and emerge in the feces. Control of pests in the feces indirectly protects the animals from the pests.

The compounds are formulated for use as ectoparasiticides in manners known to those skilled in the art. In general, a formulation will include a compound of the present invention and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

The compounds of the invention are also useful as human pharmaceuticals to control parasites, for example, lice. The compounds can be used, for example, in the formulations for controlling lice that are disclosed in WO 00/01347.

The Anoplura, or sucking lice, are parasites found on nearly all groups of mammals. Of the 15 recognized families of Anoplura, two families, Pediculidae and Pthiridae, have species found on humans. *Pediculus humanus* is the only species in the family Pediculidae that infests humans. It includes the head louse, *Pediculus humanus capitis*; and the body or clothing louse, *Pediculus humanus humanus*, sometimes called *Pediculus corporis*. The crab louse, *Pthirus pubis*, is a distinct species and is the only member of the family Pthiridae that infests humans. As used herein, the term "human lice or louse" includes a member of *Pediculus humanus* or *Pthirus pubis*.

Accordingly, in one of its aspects, the invention provides pediculicidal/ovicidal (anti-lice) formulations for controlling a lice infestation in a human comprising as an active ingredient a spinosyn, or a physiologically acceptable derivative or salt thereof, and a physiologically acceptable carrier. Especially useful formulations of this invention are hair-care formulations. Especially useful hair-care formulations are shampoos. The invention also provides methods of using these formulations to control human lice species. These formulations and methods control lice in a safer, more effective manner than previously known anti-lice formulations and methods.

The anti-lice formulations of this invention may be formulated in a number of ways. Particularly useful formulations are shampoos, conditioners, and lotions of the type disclosed in WO 00/01347.

When used in a shampoo formulation, hair conditioner formulation, or lotion the spinosyn component is present at a level of from about 0.1% to about 30%, preferably from about 1% to about 10%.

Specific embodiments contemplated include

A. A formulation for controlling a lice infestation in a human comprising as an active ingredient a compound of formula 1 or 2 where R5 is a group having one of the formulas 4a through 4i, or a physiologically acceptable derivative or salt thereof, and a physiologically acceptable carrier.

B. A formulation of embodiment A that is a hair care formulation.

C. A pediculicidal shampoo comprising:
  (a) from about 0.1% to about 30% of a compound of formula 1 or 2 where R5 is a group having one of the formulas 4a through 4i, or a physiologically acceptable derivative or salt thereof;
  (b) from about 5% to about 30% of a synthetic surfactant;
  (c) from about 1% to about 7% of an amide; and
  (d) water.

D. A shampoo of embodiment C wherein the synthetic surfactant is anionic, amphoteric, cationic, zwitterionic, or non-ionic, or a mixture thereof.

E. A shampoo of embodiment D wherein the amide is coconut monoethanolamide, coconut diethanolamide or a mixture thereof.

F. A shampoo of embodiment D additionally comprising from about 1% to about 10% of a non-volatile silicone material.

G. A shampoo of embodiment F wherein the non-volatile silicone is a polyalkyl siloxane, polyalkylaryl siloxane, polyether siloxane co-polymer, or a mixture thereof, whose viscosity is from about 100 centipoise to about 150,000,000 centipoise at 25°.

H. A shampoo of embodiment G additionally comprising from about 0.5% to about 5% of a suspending agent selected from the group consisting of crystalline amphiphilic materials having needle-like or platelet structures, polymeric materials, clays, fumed metal oxides, and mixtures thereof.

I. A shampoo of embodiment H wherein the suspending agent is a crystalline amphiphilic material selected from the group consisting of long chain $C_{16}$–$C_{22}$ acyl derivatives, long chain $C_{16}$–$C_{22}$ alkanolamide of fatty acids, and mixtures thereof.

J. A shampoo of embodiment I wherein the suspending agent is an ethylene glycol diester.

K. A shampoo of embodiment D wherein the amount of a spinosyn, or derivative or salt thereof, is at a level from about 0.25% to about 1.5%.

L. A method for controlling a lice infestation in a human comprising topically administering a formulation of embodiment A to the human.

M. The method of embodiment L wherein the lice infestation is *Pediculus humanus capitis*.

N. The method of embodiment L wherein the lice infestation is *Pediculus humanus humanus*.

O. The method of embodiment L wherein the lice infestation is *Pthirus pubis*.

P. A method for treating human hair to kill and facilitate removal of lice and their eggs comprising the steps of:
  (a) applying from about 10 g to about 30 g of a formulation comprising a compound of formula 1 or 2, where R5 is a group having one of the formulas 4a through 4i, or a physiologically acceptable derivative or salt thereof, and a physicologically acceptable carrier to wet hair;
  (b) working the formulation through the hair and scalp;
  (c) leaving the formulation on the hair and scalp for about 6–10 minutes;
  (d) removing the formulation from the hair by rinsing, with water.

Q. The use of a compound of formula 1 or 2, where R5 is a group having one of the formulas 4a through 4i, or a physiologically acceptable derivative or salt thereof, or a formulation containing either entity, for the manufacture of a medicament for controlling lice in a human.

We claim:

1. An insecticide or acaricide composition which comprises an insect, mite, or tick inactivating amount of compound of the formula (1) or (2):

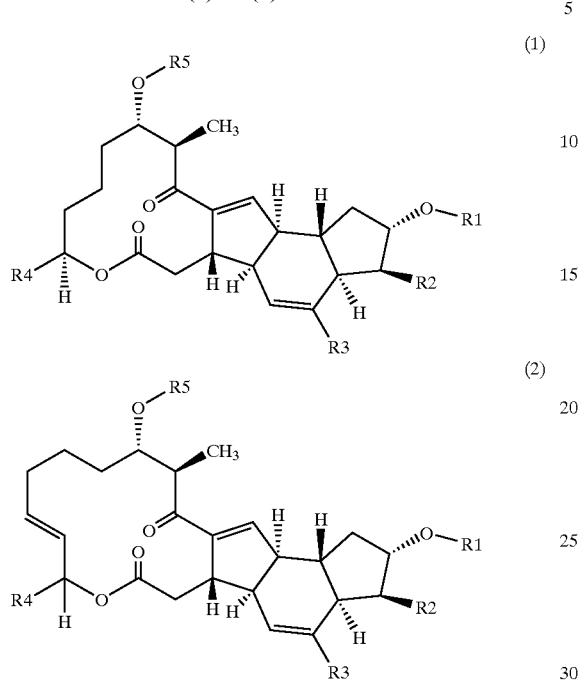

or a salt thereof, wherein

R1 is a group of formula 2a, 2b, or 2c

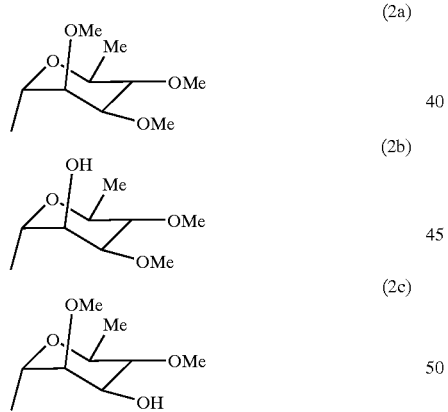

R2 is H or OH;

R3 is H or $CR_3$;

R4 in formula 1 is 1-butenyl, 1,3-butadienyl, n-butyl, 3-hydroxy-1-butenyl, or 1-propenyl; R4 in formula 2 is ethyl;

and R5 is a group having one of the following formulas 4a through 4i

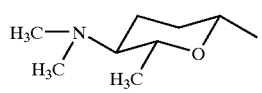

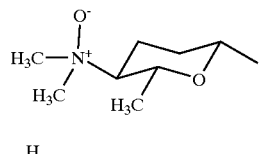

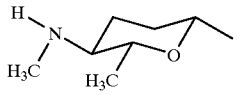

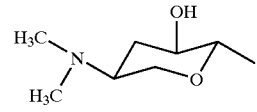

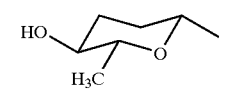

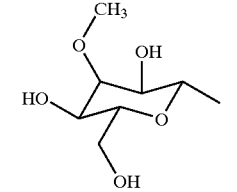

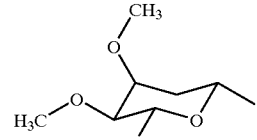

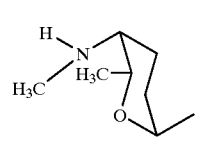

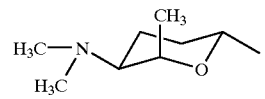

in combination with a phytologically- or physiologically-acceptable carrier.

2. An insecticide or acaricide method which comprises applying to the locus of an insect, mite, or tick inactivating amount of a compound of the formula (1) or (2):

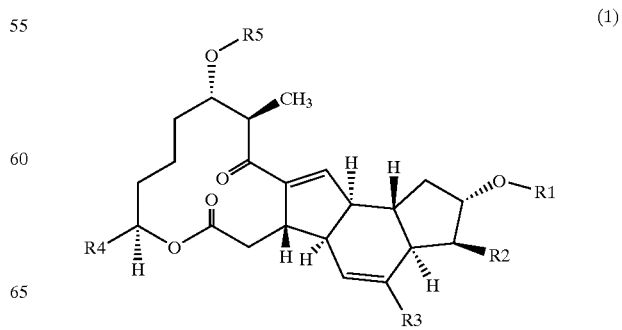

(2)

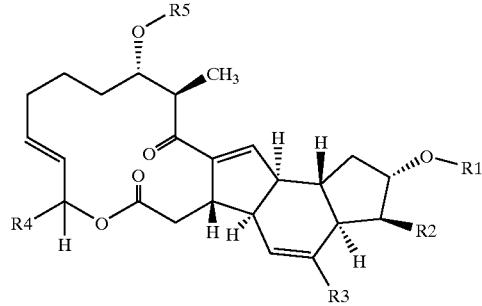

or a salt thereof, wherein

R1 is a group of formula 2a, 2b, or 2c (2a)
(2b)
(2c)

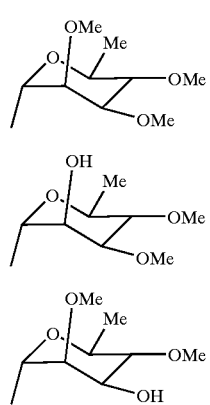

R2 is H or OH;

R3 is H or CH$_3$;

R4 in formula 1 is 1-butenyl, 1,3-butadienyl, n-butyl, 3-hydroxy-1-butenyl, or 1-propenyl; R4 in formula 2 is ethyl;

and R5 is a group having one of the following formulas 4a through 4i (4a)
(4b)
(4c)
(4d)

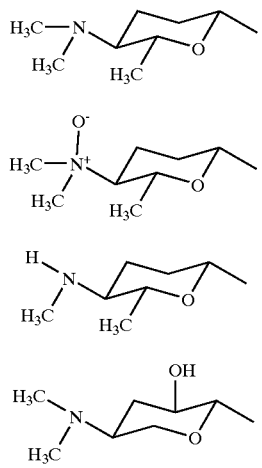

(4e)
(4f)
(4g)
(4h)
(4i)

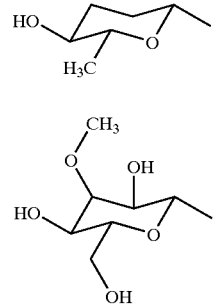
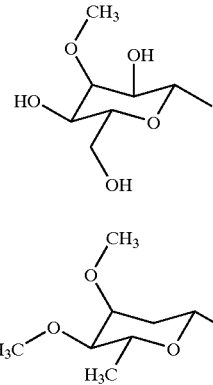
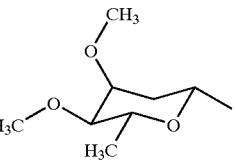
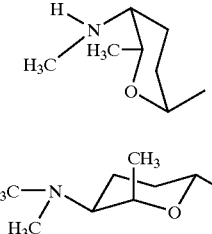
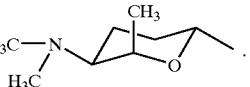

3. A method of protecting a locus from infestation by insects, mites, or ticks which comprises applying to the locus an insect, mite, or tick inactivating amount of a compound of the formula (1) or (2):

(1)

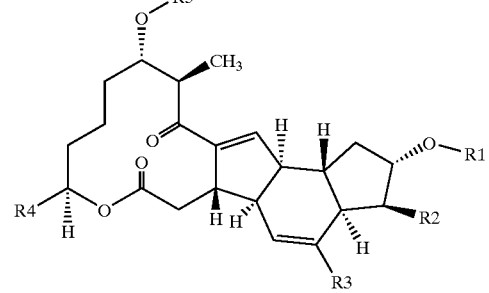

(2)

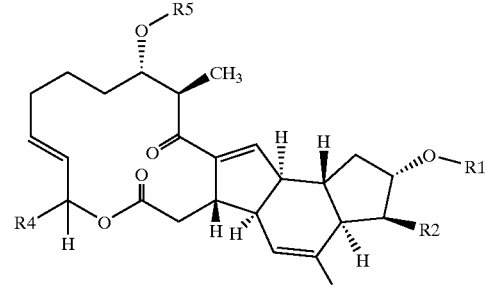

or a salt thereof, wherein

R1 is a group of formula 2a, 2b, or 2c

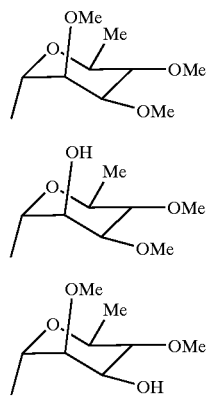

R2 is H or OH;

R3 is H or CR₃;

R4 in formula 1 is 1-butenyl, 1,3-butadienyl, n-butyl, 3-hydroxy-1-butenyl, or 1-propenyl; R4 in formula 2 is ethyl;

and R5 is a group having one of the following formulas 4a through 4i

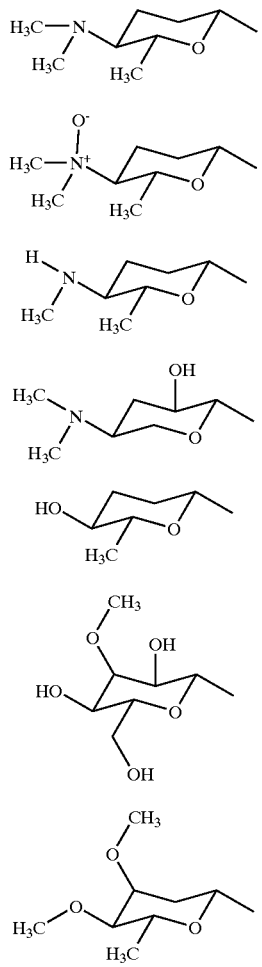

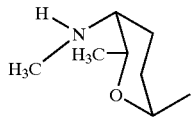

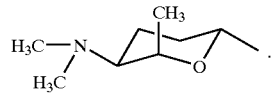

4. A method of controlling a population of parasites that infest a host animal which comprises administering to the host animal a parasiticidal amount of a compound of the formula (1) or (2):

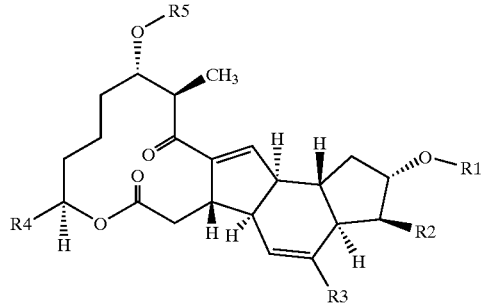

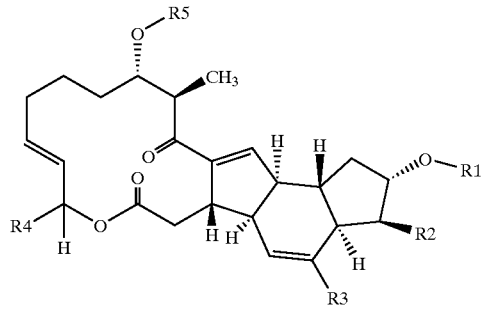

or a salt thereof, wherein

R1 is a group of formula 2a, 2b, or 2c

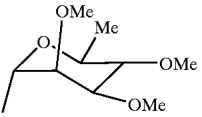

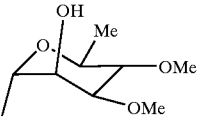

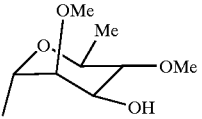

R2 is H or OH;

R3 is H or CH₃;

R4 in formula 1 is 1-butenyl, 1,3-butadienyl, n-butyl, 3-hydroxy-1-butenyl, or 1-propenyl; R4 in formula 2 is ethyl; and R5 is a group having one of the following formulas 4a through 4i (4a)

(4b)
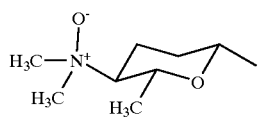

(4c)
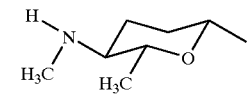

(4d)
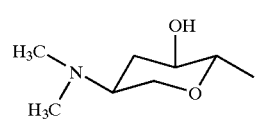

(4e)
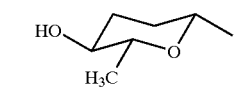

(4f)
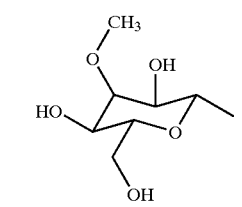

(4g)
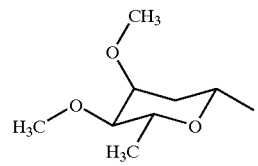

(4h)
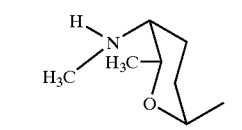

(4i)
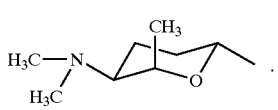

5. A formulation for controlling a lice infestation in a human comprising as an active ingredient a compound of the formula (1) or (2):

(1)
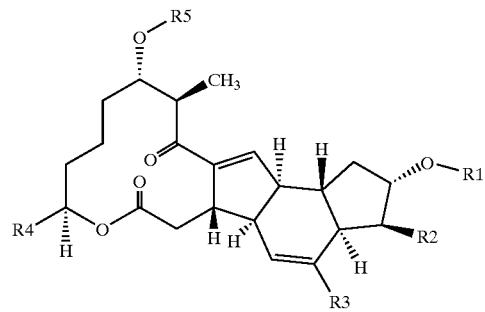

(2)
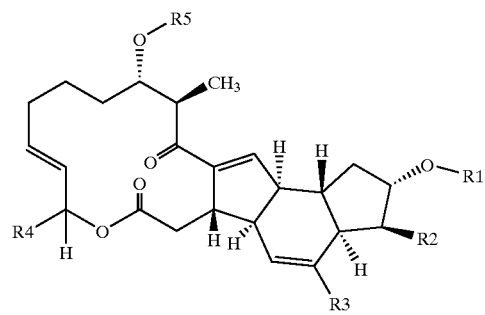

or a salt thereof, wherein
R1 is a group of formula 2a, 2b, or 2c (2a)
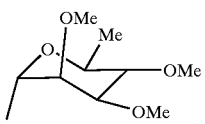

(2b)
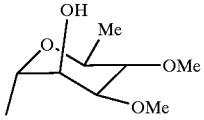

(2c)
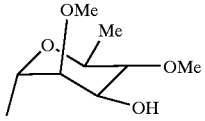

R2 is H or OH;

R3 is H or CH₃;

R4 in formula 1 is 1-butenyl, 1,3-butadienyl, n-butyl, 3-hydroxy-1-butenyl, or 1-propenyl; R4 in formula 2 is ethyl;

and R5 is a group having one of the following formulas 4a through 4i (4a)
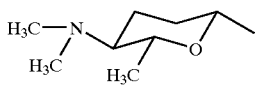

(4b)
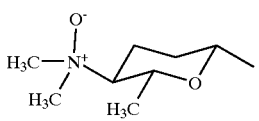

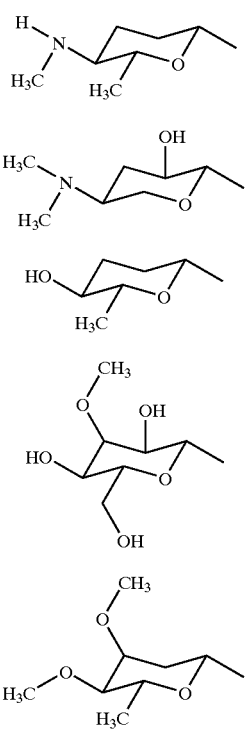
(4c)
(4d)
(4e)
(4f)
(4g)
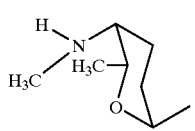
(4h)
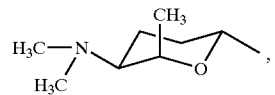
(4i)
or a physiologically acceptable derivative or salt thereof, and a physiologically acceptable carrier.
* * * * *